United States Patent [19]

Burstein

[11] Patent Number: 4,973,603

[45] Date of Patent: Nov. 27, 1990

[54] PLATELET ACTIVATING FACTOR ANTAGONIST AND METHODS OF USE THEREFOR

[76] Inventor: Sumner Burstein, 6 Knight Rd., Framingham, Mass. 01701

[21] Appl. No.: 350,391

[22] Filed: May 11, 1989

Related U.S. Application Data

[63] Continuation-in-part of Ser. No. 207,707, Jun. 16, 1988, abandoned.

[51] Int. Cl.$^5$ .............................................. A61K 31/35
[52] U.S. Cl. .................................... 514/454; 514/822
[58] Field of Search ....................... 514/455, 822, 454

[56] References Cited

PUBLICATIONS

Chem. Abst. 79:49530t, 1973.
Chem. Abst. 87:48575q, 1977.
Chem. Abst. 88:58994k, 1978.
Chem. Abst. 100:133678g, 100:133680b, and 100:133681c, 1984.
E. A. Formukong et al., *J. Pharm. Pharmacol,* 39(Suppl.): p. 79P (1987).
E. A. Formukong et al., *Br. Journal of Pharmacol.,* 92 (Suppl.): p. 601P (1987).
S. Burstein et al., *Biochem. Pharmacol.,* 35(15):2553–2558 (1986).
R. S. Wilson et al., *J. Medical Chemistry,* 18(7):700–703 (1975).
H. M. Bhargava, *Gen. Pharmacol.,* 9(4):195–213 (1978).
D. Heiden et al., *Thrombosis Res.,* 17:885–889 (1980).
J. F. Rivas et al., *Eur. J. Pharmacol.,* 65:317–318 (1980).
H. DeSousa et al., *Japan J. Pharmacol.,* 28:507–510 (1978).
F. H. Chilton et al., *Journal of Biological Chemistry,* 257:5402–5407 (1982).
P. Braquet et al., *Pharmacol. Revs.,* 392:97–145 (1987).
R. Mechoulam et al., *Experimentia,* 29:1193–1195 (1973).
W. Calhoun et al., *Agents and Actions,* 21:306–309 (1987).
J. M. Young et al., *Prostaglandins,* 30(4):545–551 (1985).

*Primary Examiner*—John W. Rollins
*Attorney, Agent, or Firm*—Hamilton, Brook, Smith & Reynolds

[57] ABSTRACT

6a,7,10,10a-tetrahydro-6,6-dimethyl-9-carboxyl-3-pentyl-6-H-dibenzo [b,d] pyran-1-ol is a potent antagonist to endogenous platelet activating factor (PAF). PAF is a factor in many of the pathological manifestations of disease, allergy or injury, such as inflammation, thrombosis and anaphylaxis. The actions of PAF can be inhibited in vivo by the present composition, thereby providing a safe and effective treatment for PAF-induced disorders.

9 Claims, No Drawings

PLATELET ACTIVATING FACTOR ANTAGONIST AND METHODS OF USE THEREFOR

GOVERNMENT SUPPORT

Work described herein was supported in part by grants from the National Institute of Drug Abuse.

RELATED APPLICATIONS

This application is a continuation-in-part of U.S. Ser. No. 07/207,707, filed Jun. 16, 1988, now abandoned.

BACKGROUND OF THE INVENTION

Platelet activating factor (PAF) has been identified as 1-0-alkyl-2-0-acetyl-sn-glycero-3-phosphocholine. Many different types of mammalian cells have been reported to release PAF upon stimulation. F. H. Chilton et al., *Journal of Biochemistry*, 257:5402–5407 (1982).

Platelet activating factor (PAF) is an endogenous lipid which has been implicated in a number of adverse pathological consequences due to disease and/or environmental occurrences. P. Braquet, L. Touqui, T. Y. Shen and B. B. Vargaftig, *Pharmacol. Revs.* 39:97–145(1987). These include platelet-induced thrombosis, acute inflammation, asthma and systemic anaphylaxis, transplant rejection, cardiac anaphylaxis, kidney physiology and immune disorders, endotoxic and IgG-induced shock, gastrointestinal ulceration, inflammatory and allergic skin diseases, retinal and corneal diseases, neuronal degradation, panic disorders and failure of ovoimplantation. An intensive search has been in progress in recent years to discover and develop drugs which will effectively control these adverse effects of PAF. Thus far, no agents of this type have been made available for general use in treating PAF-induced medical problems.

SUMMARY OF THE INVENTION

This invention relates to the discovery that 6a,7,10,10a-tetrahydro-6,6-dimethyl-9-carboxyl-3-pentyl-6H-dibenzo[b,d]pyran-1-ol is a potent antagonist to the actions of PAF. A composition containing this compound is administered to a subject for treatment of various disorders induced by PAF. The composition can be used as a therapeutic agent for the treatment of PAF-mediated disorders such as asthma or other pulmonary dysfunction, systemic anaphylaxis, transplanted organ rejection, septic shock, gastrointestinal ulceration, allergic skin diseases, and acute inflammation. The composition of the invention can be administered orally or parenterally to a subject in an amount sufficient to substantially inhibit the actions of PAF, thereby reducing the symptoms caused by PAF. When administered directly into the stomach, the present composition is non-ulcerogenic, and thus does not induce the gastrointestinal damage which accompanies the chronic use of PAF antagonists currently available.

DETAILED DESCRIPTION OF THE INVENTION

For the purposes of the present invention, 6a,7,10,10a-tetrahydro-6,6-dimethyl-9-carboxyl-3-pentyl-6H-dibenzo[b,d]pyran-1-ol includes the molecule having the structure shown in Formula I, and all analogs thereof:

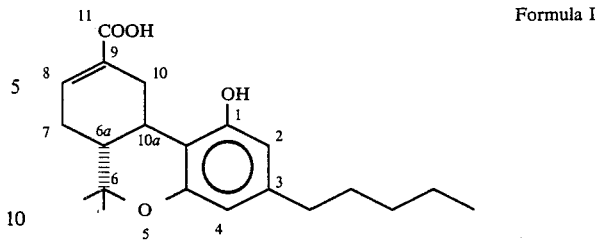

Formula I

The term "Formula I" will be used hereinafter to designate the molecule and its analogs. As used herein, the term "analog" means a chemically related structure which has the biological effects produced by the compound of Formula I. An analog of Formula I, for example, may have a modification in one or more of the rings, and/or one or more of its substitutes, alone or in combination. Analogs include double-bond isomers, reduction products, side-chain modifications and stereoisomers of any of the preceding molecules.

Formula I is a naturally occurring derivative of the compound 6a,7,10,10a-tetrahydro-6,6,9-trimethyl-3-pentyl-6H-dibenzo[b,d]pyran-1-ol which is a minor component of *Cannabis sativa*. R. Mechoulam, Z. Ben-Zvi, S. Agurell, I. M. Nilson, J. L. G. Nilson, H. Edery and Y. Grunfeld, *Exper.* 29:1193–1195 (1973). Formula I is formed from this compound by a series of biotransformations mediated primarily by mammalian liver enzymes.

One common adverse effect of the consumption of currently available PAF antagonists, such as naproxen and phenidone, is gastrointestinal damage, generally manifested as bleeding and/or frank ulceration. A frank ulcer is a necrotic lesion, usually elongated, which penetrates the gastric mucosa and resists removal by wiping or rinsing with physiological saline. The composition of this invention is non-ulcerogenic. In a standard pharmacological assay for ulcerogenicity, it was shown that Formula I did not induce ulcer formation. Administration of the present composition directly into the stomach did not result in ulcer formation in any rats to which it was given. This result is in contrast to the effects of aspirin, which, when given in half the therapeutic dose, induced the formation of gastric lesions in each test animal.

The present composition can be used in both veterinary medicine and in human therapy. The composition can be administered orally or parenterally. The form in which the drug will be administered will depend on the route by which it is administered. In one embodiment, the drug is dissolved in a vegetable oil, such as olive oil or peanut oil, and, optionally, encapsulated in a gelatin capsule. For human therapy, a preferred method of administering Formula I is orally, in the form of a gelatin capsule. The dosage of the metabolite according to this invention is generally between about 10 to 500 mg/70 kilograms (kg) of body weight per day, preferably 50 to 150 mg/70 kg/day. The actual preferred amounts of active compound in a specific case will vary, according to the particular species of mammal afflicted, the severity of the affliction and the actual method of administration. In general, the composition of the present invention is administered to an individual periodically as necessary to improve symptoms of the disease being treated. The length of time during which the drugs are administered and the dosage will depend upon the disease being treated, the type and severity of the symptoms, and the physical condition of the subject being treated.

The composition of the present invention, or a synthetic analog thereof, can be administered to an afflicted mammal in the form of a composition comprising an effective PAF-antagonizing amount of Formula I in a pharmacologically acceptable carrier, for example, a gelatin capsule, or edible oil (e.g., a vegetable oil) for oral administration, or sterile saline solution for parenteral administration. A composition to be administered orally in tablet form can include, in addition to the drug, a filler (e.g., lactose), a binder (e.g., carboxymethyl cellulose, gum arabic, gelatin), an adjuvant, a flavoring agent, a coloring agent, and a coating material (e.g., wax or plasticizer). Those skilled in the art will know, or will be able to ascertain with no more than routine experimentation, appropriate pharmacological carriers for said composition.

This invention has further applications in the area of medicinal chemistry, where Formula I can be used as a model to design similar or more efficacious analogs and compounds for antagonizing the action of PAF in mammals. An analog is a compound that resembles another in structure, as defined hereinabove. For example, an analog of Formula I may have a modification in one or more of the rings and/or one or more of its substituents, alone or in combination.

The invention is illustrated further by the following exemplification, which is not to be taken as limiting in any way.

Exemplification

Chemicals 6a,7,10,10a-tetrahydro-6,6-dimethyl-9-carboxyl-3-pentyl-6H-dibenzo[b,d]pyran-1-ol was obtained from the Research Triangle Institute (Research Triangle Park, N.C.). The purity of the compound was monitored by reversed phase thin-layer chromatography before experimentation. Naproxen, phenidone indomethacin, and PAF were purchased from Sigma Chemical Co. (St. Louis, Mo.).

PAF Induced Paw Edema in the Mouse

The experimental procedure was adapted from Calhoun et al., *Agents & Actions*, 21:306–309 (1987). Charles River CD-1 female mice (20–25 G) were given a dose of Formula I, or phenidone, using peanut oil as a carrier. Control mice were given doses of the carrier alone. The drugs were administered orally in a 50 $\mu$l volume of peanut oil. One hour later, 1.0 $\mu$g of PAF dissolved in 50 $\mu$l of 5% ethanol-saline was injected subcutaneously into the plantar surface of the right hind paw. The volume of this injected foot to the level of the lateral malleous was measured by water displacement immediately before drug administration and again 15 minutes after PAF injection.

The effectiveness of each compound was analyzed in the following manner. The individual paw volumes were compared by a paired t test analysis in which predrug paw volumes were compared to paw volumes 15 minutes after PAF injection to determine the level of statistical significance. The percent inhibition of edema volume was obtained from the ratio of the mean predrug volume to the mean volume after PAF. The results are shown in Table I, below. When administered in a dose of 40 mg/kg, Formula I inhibited paw edema by 46.2%. A comparable dose of phenidone, an agent reported to be effective against PAF edema by Calhoun et al. in *Agents & Actions*, 21:306–309 (1987), produced 20.4% inhibition of edema (Table I). These results demonstrate that Formula I is an effective antagonist to the inflammatory actions of PAF.

TABLE I

| PAF[1]-INDUCED PAW EDEMA IN THE MOUSE | | | |
|---|---|---|---|
| Treatment | Dose (mg/kg)[2] | % Inhibition of Edema | P(N)[4] |
| Formula I | 40 | 46.2 | 0.001 (10) |
| Formula I | 20 | 50.2 | 0.0002 (10) |
| Formula I | 10 | 21.8 | 0.032 (10) |
| Phenidone | 80 | 35.7 | 0.0079 (5) |
| Phenidone | 40 | 20.4 | 0.089 (10) |

[1]Platelet activating factor (1 ug/paw) in 5% ethanol-saline (0.05 ml); volume change measured 15 min later by water displacement.
[2]Drugs administered orally in peanut oil (0.05 ml) 1 hour prior to PAF injection.
[3]Decrease in edema volume (corrected for PAF vehicle) when compared to drug vehicle controls. Oil treated controls ranged from 49 to 56 $\mu$l.
[4]Probability derived from a t test. N = number of mice tested.

PAF Induced Mortality

The induction of mortality by the injection of low doses of PAF into mice has been described as a method for assessing the effectiveness of agents to antagonize the anaphylactic properties of PAF by J. M. Young, P. J. Maloney, S. W. Jubb and J. S. Clarke, in *Prostaglandins*, 30:545–551 (1985). Charles River CD-1 female mice (25–30 g) were given intraperitoneal injections of PAF (10 $\mu$g) dissolved in 100 $\mu$l of 5% ethanol-saline. The drugs tested were Formula I, naproxen, and phenidone. Test drugs were orally administered in 50 $\mu$l of peanut oil one hour prior to PAF injection. Control mice were dosed with vehicle only. Mortality was assessed by counting survivors at one hour, two hours, and twenty four hours after the PAF injection.

The data in Table II show that under these conditions, vehicle-treated control mice showed a 32% survival at all time points. The protective effect of Formula I is clearly shown at a dose of 40 mg/kg, which resulted in an 80% survival rate at all time points. The other agents, phenidone and naproxen, were less protective than Formula I, particularly at longer time intervals, as shown in Table II. These data illustrate that Formula I is a potent antagonist to the anaphylactic effects of PAF.

TABLE II

| PAF Induced Mortality[1] | | | | |
|---|---|---|---|---|
| | | Survivors/N(%)[3] | | |
| Treatment[2] | Dose(mg/kg) | 1 hr | 2 hrs | 24 hrs |
| Vehicle Only | — | 8/25(32) | 8/25(32) | 8/25(32) |
| Formula I | 80 | 7/10(70) | 7/10(70) | 7/10(70) |
| Formula I | 40 | 12/15(80) | 12/15(80) | 12/15(80) |
| Formula I | 20 | 5/20(25) | 5/20(25) | 5/20(25) |
| Phenidone | 40 | 1/5(20) | 1/5(20) | 1/5(20) |
| Naproxen | 40 | 5/5(100) | 3/5(60) | 3/5(60) |
| Naproxen | 20 | 4/10(40) | 4/10(40) | 2/10(20) |

[1]Female CD-1 mice (25–30 g) were injected intraperitoneally with PAF (10 $\mu$g) dissolved in 5% ethanol-saline.
[2]All drugs were administered orally in peanut oil (50 $\mu$l) one hour prior to PAF injection.
[3]N = total number of mice treated.

The Rat Ulcerogenicity Test

A quantitative assessment of experimentally induced acute gastric erosions and ulcers is crucial since their extent may be an indication of the ulcerogenic potential of pharmacologic agents. Robert and Szabo, In: *Selye's*

*Guide to Stress Research*, (Vol. 2, A. Selye, Ed.) New York; Van Nostrand Reinhold Co., pp. 22–46 (1983); and Robert et al., *Gastroenterology*, 77:433–443 (1979). Experimental groups of 5–11 rats (Charles River CD) were fasted for 24 hours before the administration of either aspirin, Formula I or indomethacin by a rubber stomach tube (Rusch No. 8). The animals were killed 1 hour later by carbon dioxide asphyxiation. At that time, 4 ml of 10% aqueous buffered formaldehyde (formalin) was injected directly into the stomach of each animal. This in situ intraluminal fixation with formalin was especially critical for the assessment of small gastric erosions induced by aspirin since the overlying hemorrhage could easily be removed by rinsing the unfixed stomach. After 5 minutes of in situ fixation, the stomach and proximal duodenum were removed, opened along the greater curvature, pinned on a cork with mucosa upward, and immersed in 10% formaldehyde until further processing. Szabo, S. et al., *J. Pharmacol. Meth.*, 13:59–66 (1985). The gastric lesions were then evaluated by direct visual inspection.

For comparative purposes, a semiquantitative scale of 0–3 was used to assess the extent of gastric mucosal lesions. Szabo et al., *Science*, 214:200–202 (1981); and Szabo et al., *Gastroenterology*, 85:1384–1390 (1983). According to this scale, a score of 0 indicates a normal mucosa; 1 represents the appearance of between 1 and 4 small petechiae; 2 indicates the presence of 5 or more petechiae or hemmorhagic streaks up to 4 mm in length; 3 represents the appearance of erosions longer than 5 mm or confluent hemmorrhages.

The results from this study, shown in Table III, indicate that Formula I, when directly administered in an amount twice its therapeutic dose in the mouse (40 mg/kg), does not induce the formation of gastric lesions. However, when only half the therapeutic amount of aspirin (100 mg/kg) was administered, each of the experimental animals experienced gastrointestinal damage.

TABLE III

| The Rat Ulcerogenicity Test | | | |
|---|---|---|---|
| Substance | Dose[1] | Incidence[2] | Mean Score |
| Aspirin | 100 | 10/10 | 1.9 |
| Formula I | 80 | 0/10 | 0.0 |
| Indomethacin | 20 | 6/11 | 0.77 |
| Indomethacin | 10 | 2/5 | 0.6 |

[1]mg/kg
[2]Number of rats with lesions/total tested.

The Mouse Ear Edema Test

The direct application of arachidonic acid to skin, such as the mouse ear, produces an edematous response which is believed to be mediated by eicosanoids resulting from the actions of both cyclooxygenase and lipoxygenase systems. J. M. Young, D. A. Spires, C. J. Bedford, B. Wagner, S. J. Ballaron and L. M. DeYoung, *J. Invest. Dermatol.* 82:367–371 (1984); E. E. Opas, R. J. Bonney, and J. L. Hanes *J. Invest. Dermatol.* 84:253–256 (1985). PAF has been reported to cause the release of arachidonic acid, and as a result, gives rise to increased levels of eicosanoids in the exposed tissues. F. H. Chilton, J. T. Flaherty, C. E. Walsh, M. J. Thomas, R. L. Wykle, L. R. DeChatelet and B. M. Waite, *J. Biol. Chem.*, 257:5402–5407 (1982). Thus, the mouse ear edema test can be used to discover substances which antagonize the effects of PAF. Such agents which act on both cyclooxygenase and lipoxygenase have been referred to as "dual inhibitors".

The drugs tested were Formula I, naproxen, indomethacin and phenidone. The test drugs were dissolved in 10 μl ethanol and applied to the inner surface of the left ears of Charles River CD-1 female mice. Control values were obtained by applying 10 μl of ethanol to the right ear so that each mouse served as its own control. One hour later, arachidonic acid (0.5 mg/ear in 10 μl ethanol) was applied to both ears and allowed to act on the skin for one hour. The mice were then killed by cervical dislocation and the ears removed so that all tissue samples were of equivalent areas. The extent of edema in each sample was measured by weighing on an analytical balance.

The results, shown in Table IV, show that Formula I is effective in reducing arachidonic acid-induced skin edema. Formula I displays approximately one half the potency of agents such as indomethacin and phenidone, however, it is more active than the widely used antiinflammatory drug naproxen.

TABLE IV

| THE MOUSE EAR EDEMA TEST | | | |
|---|---|---|---|
| Treatment | Dose (mg/ear)[1] | % Inhibition of Edema[2] | p(N)[3] |
| Formula I | 1.0 | 19.3 | 0.029(5) |
| Formula I | 0.50 | 19.1 | 0.012(5) |
| Formula I | 0.25 | 18.3 | 0.034(5) |
| Formula I | 0.13 | 0.6 | 0.624(5) |
| Naproxen | 1.0 | 5.8 | 0.144(5) |
| Indomethacin | 0.10 | 21.8 | 0.019(5) |
| Indomethacin | 0.05 | 24.1 | 0.0012(5) |
| Phenidone | 0.25 | 24.4 | 0.006(5) |
| Phenidone | 0.13 | 26.6 | 0.007(5) |
| Phenidone | 0.063 | 15.4 | 0.054(5) |

[1]The drug was dissolved in ethanol (10 μl) and applied to the inner surface of the left ear; ethanol (10 μl) was applied to the right ear. After one hour, arachidonic acid (0.5 mg in 10 μl ethanol) was applied to both ears. One hour later the mice were sacrificed and ear weights obtained.
[2]These values were calculated by comparing left and right ear weights with a control group which received arachidonic acid on the left ear only (mean of left ears = 44.80 ± 6.91 mg; mean of right ears = 25.30 ± 5.04 mg; p = 0.011).
[3]Significance was determined using a paired t test; N = number of mice.

Inhibition of 5-HETE Synthesis

It has been proposed that products of lipoxygenase action such as leukotriene by ($LTB_4$) and 5-hydroxyeicosatetraenoic acid (5-HETE) can act synergistically with PAF to cause neutrophil degranulation which may contribute to the development of inflammation. J. T. O'Flaherty, *J. Cell Biology*, 122:229–239 (1985). Formula I was tested as an inhibitor of 5-HETE production in mouse peritoneal macrophages using the following procedure.

Peritoneal cells were collected from female CD-1 mice (20–25 g) following sacrifice by cervical dislocation. The cells from each group of mice were pooled, centrifuged and suspended in MEM. Aliquotes containing $4.5 \times 10^6$ cells in 3.0 ml MEM were placed in culture dishes and incubated for 18 hours at 37° C. By this procedure, a relatively homogenous monolayer of macrophages was obtained. Eicosanoid synthesis was brought about by the addition of $^{14}C$-arachidonic acid ($2 \times 10^5$ dpm; 0.22 μM) followed by a calcium ionophore, A23187 (0.03 μM). After 15 minutes, the reaction was stopped by the addition of citric acid to pH4 and the products were extracted with ethyl acetate. Silica gel thin layer chromatography (hexane; ether; acetic acid; 50:50:1) was used to separate the 5-HETE which was identified by comparison with authentic material. Carbon-14 content was measured by liquid scintillation counting of the HETE containing zone. The significance of drug induced changes was calculated using the Student's test when compared with vehicle treated (ethanol, 30 μl) cells.

The data shown in Table V show that Formula I over the dose range of 3.2 to 8 μM reduces 5-HETE synthesis to one half of the control level in a statistically significant manner. This provides supporting evidence for the in vivo antiinflammatory effects demonstrated for Formula I.

TABLE V

INHIBITION OF 5-HETE SYNTHEIS BY THC-7 OIC ACID IN MOUSE MACROPHAGES

| Treatment (μM) | 5-HETE (%)[1] | p[2] | % Inhibition |
|---|---|---|---|
| Vehicle (EtOH, 10 μl) | 2.9 ± 0.16 | — | — |
| Formula I (16) | 3.10 ± 0.10 | 0.03 | — |
| Formula I (8) | 1.48 ± 0.87 | 0.015 | 49 |
| Formula I (4) | 1.68 ± 0.15 | 0.0008 | 42 |
| Formula I (3.2) | 1.58 ± 0.41 | 0.003 | 46 |
| Formula I (1.6) | 3.03 ± 0.42 | 0.25 | — |
| Formula I (0.32) | 3.08 ± 0.36 | 0.11 | — |

[1] Values represent the percentage of total recovered radioactivity.
[2] Probability values calculated by the Student't test.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A method for treating mammals afflicted with PAF-induced disorders comprising administering to the mammal a therapeutically effective amount of 6a,7,10,-10a-tetrahydro-6,6-dimethyl-9-carboxyl-3-pentyl-6H-dibenzo[b,d]pyran-1-ol or a biologically functional analog thereof, in a pharmaceutically acceptable carrier.

2. A method of claim 1 wherein the PAF-induced disorders are selected from the group consisting of asthma, pulmonary dysfunction, systemic anaphylaxis, transplanted organ rejection, septic shock, allergic skin diseases, acute inflammation, platelet-induced thrombosis, cardiac anaphylaxis, psoriasis, gastrointestinal ulceration, neuronal degeneration, failure of ovoimplantation, kidney physiology and immune disorders, retinal and corneal diseases, and panic disorders.

3. A method of claim 1 wherein the therapeutically effective amount of 6a,7,10,10a-tetrahydro-6,6-diemthyl-9-carboxyl-3-pentyl-6H-dibenzo[b,d]pyran-1-ol administered to the mammal is from about 10 mg/70 kg/day to about 500 mg/70 kg/day.

4. A method of claim 1 wherein the therapeutically effective 6a,7,10,10a-tetrahydro-6,6-dimethyl-9-carboxyl-3-pentyl-6H-dibenzo[b,d]pyran-1-ol administered to the mammal is from about 50 mg/70 kg/day to about 150 mg/ 70 kg/day.

5. A method of claim 1 wherein the pharmaceutically acceptable carrier is selected from the group consisting of gelatine and edible oils.

6. A method of claim 5 wherein the 6a,7,10,10a-tetrahydro-6,6-dimethyl-9-carboxyl-3-pentyl-6H-dibenzo[b,d]pyran-1-ol is administered orally.

7. A method of claim 1 wherein the pharmaceutically acceptable carrier is sterile saline.

8. A method of claim 7 wherein the 6a,7,10,10a-tetrahydro-6,6-dimethyl-9-carboxyl-3-pentyl-6H-dibenzo[b,d]pyran-1-ol is administered parenterally.

9. An improved method for treating PAF-induced disorders in mammals wherein a PAF-antagonist is administered to said mammal wherein the improvement comprises administering to said mammal an effective PAF-antagonizing amount of 6a,7,10,10a-tetrahydro-6,6-dimethyl-9-carboxyl-3-pentyl-6H-dibenzo[b,d]pyran-1-ol or an analog thereof.

* * * * *